United States Patent [19]

Vanlerberghe et al.

[11] 4,349,532
[45] Sep. 14, 1982

[54] COSMETIC COMPOSITIONS BASED ON POLY-(QUATERNARY AMMONIUM) POLYMERS

[76] Inventors: Guy Vanlerberghe, 40 Rue du General de Gaulle, Villevaude 77410 Claye Souilly; Henri Sebag, 26 Rue Erlanger, 75016 Paris; Alexandre Zysman, 6, Rue George Eastman, 75013 Paris, all of France

[21] Appl. No.: 942,319

[22] Filed: Sep. 14, 1978

[30] Foreign Application Priority Data

Sep. 20, 1977 [LU] Luxembourg ............................ 78153

[51] Int. Cl.³ ........................ A61K 7/06; A61K 7/09; A61K 7/11; A61K 7/13
[52] U.S. Cl. ......................................... 424/47; 8/405; 8/406; 8/407; 424/DIG. 4; 424/70; 424/71; 424/72; 424/78; 424/80; 424/81; 528/335
[58] Field of Search ........................... 424/70; 528/335

[56] References Cited

U.S. PATENT DOCUMENTS

| | | | |
|---|---|---|---|
| 3,671,468 | 6/1972 | Tsuda et al. ........................ | 528/335 |
| 3,917,817 | 11/1975 | Vanlerberghe et al. .............. | 424/70 |
| 3,958,581 | 5/1976 | Abegg et al. ...................... | 424/70 X |
| 4,013,787 | 3/1977 | Vanlerberghe et al. .............. | 424/70 |

FOREIGN PATENT DOCUMENTS

| | | | |
|---|---|---|---|
| 2044024 | 3/1971 | Fed. Rep. of Germany ........ | 424/70 |
| 1484601 | 5/1967 | France ................................ | 424/70 |
| 2128507 | 10/1972 | France ................................ | 424/70 |
| 2270846 | 12/1975 | France ................................ | 424/70 |
| 2270851 | 12/1975 | France ................................ | 424/70 |
| 2316271 | 1/1977 | France ................................ | 424/70 |
| 2333012 | 6/1977 | France ................................ | 424/70 |
| 1288006 | 9/1972 | United Kingdom .................. | 424/70 |
| 1410581 | 10/1975 | United Kingdom .................. | 424/70 |

OTHER PUBLICATIONS

Makromal, Chem. 1977, vol. 178, pp. 2573–2580.

*Primary Examiner*—Dale R. Ore
*Attorney, Agent, or Firm*—Fleit & Jacobson

[57] ABSTRACT

Composition suitable for treating the hair or skin, which conains at least one poly-(quaternary ammonium) polymer having units of the formula:

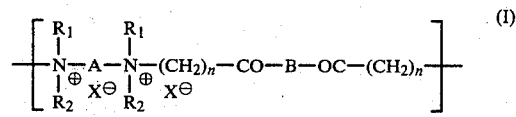

in which
A denotes an alkylene, hydroxyalkylene, alkenylene or alkynylene radical;
B denotes:
  (a) —O—Z—O— in which Z denotes a hydrocarbon radical or a group

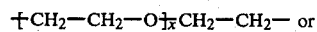

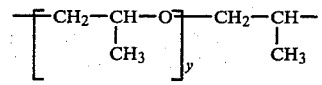

in which x and y denote a number from 1 to 4;
  (b) a bis-secondary diamine radical;
  (c) a radical —NH—Y—NH— in which Y denotes a hydrocarbon radical or the radical —CH₂—CH₂—S—S—CH₂—CH₂—; or
  (d) a group —NH—CO—NH—;
R₁ denotes C₁–C₄ alkyl; R₂ denotes a hydrocarbon radical or two R₂ radicals can complete a radical

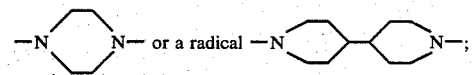

X denotes a halide; and n is 1 or an integer from 3 to 10.

The polymers used in the composition of the invention have a good compatibility with anionic surface-active agents, are degradable and do not accumulate on the hair.

51 Claims, No Drawings

COSMETIC COMPOSITIONS BASED ON POLY-(QUATERNARY AMMONIUM) POLYMERS

BACKGROUND OF THE INVENTION

1. Field of the Invention

The present invention relates to cosmetic compositions containing one or more poly-(quaternary ammonium) polymers, to polymeric compounds used in these compositions and to a process for treating the hair or skin using these compositions and compounds.

It has already been proposed to use cationic polymers, and, more particularly, polymers containing quaternary ammonium groups, as conditioning agents for the head of hair.

2. Description of the Prior Art

Compositions of this kind are described, in particular in French Pat. Nos. 2,270,846 and 2,316,271 (U.S. patent application Ser. No. 577,836, filed May 15, 1975 and U.S. patent application Ser. No. 702,924, filed July 6, 1976 now abandoned.

SUMMARY OF THE INVENTION

Cationic polymers are known to exhibit a high affinity for keratin fibers such a hair, because of the interaction of their ammonium groups with the anionic groups in the hair.

These polymers deposit on the hair all the more easily when the latter is more sensitised, and the affinity for the hair is frequently such that the polymers strongly resist removal by shampoos, brushing or treatment with an alkaline solution.

However, it has been found that, although the use of cationic polymers of this kind possesses numerous advantages inasmuch as they make the hair easier to comb out and to treat and impart springiness and a glossy appearance to the hair, these polymers tend to accumulate on the hair following repeated applications, because of their affinity for keratin.

Furthermore, these cationic polymers containing quaternary groups frequently have poor compatibility with anionic surface-active agents, which reduces the possibilities for using them and necessitates their use in two-stage treatments, before or after shampooing.

It has now been found according to the present invention that certain poly-(quaternary ammonium) polymers do not exhibit the above referred to disadvantages. In particular, these polymers can be used in one-stage treatments by virtue of their compatibility with anionic surface-active agents, they produce a conditioning effect, and they can be removed from the head of hair with conventional hair treatments.

The present invention provides a cosmetic composition suitable for treating hair or skin which contains at least one poly-(quaternary ammonium) polymer having units of the formula:

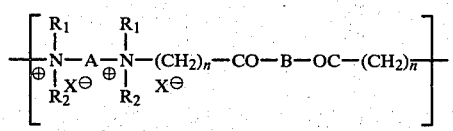

in which:

A denotes a divalent, linear or branched, saturated or unsaturated hydrocarbon group which is unsubstituted or substituted by one or more hydroxyl groups; more particularly, A denotes a linear or branched alkylene, hydroxyalkylene, alkenylene or alkynylene radical;

B denotes:

(a) a glycol radical of the formula —O—Z—O— in which Z denotes a linear or branched hydrocarbon radical or a group of the formula: —(CH$_2$—CH$_2$—O)$_x$—CH$_2$—CH$_2$— or

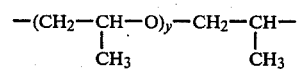

in which each of x and y denotes an integer from 1 to 4, representing a fixed degree of polymerization, or a number from 1 to 4, representing a mean degree of polymerization;

(b) a bis-secondary diamine radical such as a piperazine derivative of the formula:

(c) a bis-primary diamine radical of the formula —NH—Y—NH— in which Y denotes a linear or branched hydrocarbon radical or the divalent radical —CH$_2$—CH$_2$—S—S—CH$_2$—CH$_2$—; or (d) a ureylene group of the formula —NH—CO—NH—;

R$_1$ denotes an alkyl radical containing from 1 to 4 carbon atoms, preferably a methyl radical;

R$_2$ denotes a linear or branched hydrocarbon radical, or two adjacent R$_2$ radicals are joined together to form, together with A and the two nitrogen atoms, a divalent radical of the formula:

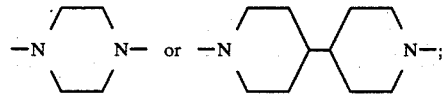

X$^\ominus$ denotes a halide ion, in particular, a bromide or chloride ion;

and n denotes 1 or an integer from 3 to 10.

A preferably denotes an alkylene, hydroxyalkylene, alkenylene or alkynylene radical having from 2 to 10 carbon atoms and more particularly denotes an ethylene, propylene, methylpropylene, butylene, methylbutylene, hexamethylene, octamethylene, decamethylene, hydroxypropylene, butenylene or butynylene radical.

The hydrocarbon radicals represented by Z and Y are preferably alkylene radicals having from 2 to 10 carbon atoms and more particularly ethylene, propylene, 2,2-dimethylpropylene, butylene, hexamethylene, octamethylene or decamethylene radicals.

The hydrocarbon radical represented by R$_2$ generally denotes an alkyl radical containing from 1 to 12 carbon atoms and preferably denotes a methyl, ethyl, propyl, isopropyl, butyl, hexyl, octyl, decyl or dodecyl radical.

Some of the polymers used in the compositions according to the present invention are new and represent a further embodiment of the present invention. These novel polymers have units of the formula:

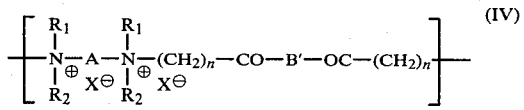 (IV)

in which B′ denotes a bis-secondary diamine radical of the formula:

or a ureylene radical of the formula —N-H—CO—NH—, n denotes 1 or an integer from 3 to 10 provided that, when B′ denotes

n denotes a number from 3 to 10, and $R_1$, $R_2$, A and X are as defined for the formula I.

The polymers used in the compositions according to the invention are suitably prepared, in accordance with a process which is in itself known, by the polycondensation of a bis-tertiary diamine, of the formula

 (II)

with a bis-halogenoacyl compound of the formula:

$$X—(CH_2)_n—CO—B—OC—(CH_2)_n—X \quad (III)$$

In these formulae, $R_1$, $R_2$, A, X, B and n are as defined above.

These polycondensation reactions are preferably carried out in customary solvents such as water, dimethylformamide, alcohols, preferably alcohols having from 1 to 4 carbon atoms, such as methanol, ethanol, isopropanol or t-butanol, or ether-alcohols such as methoxy-, ethoxy- or butoxy-ethanol, or a mixture of two or more of these solvents, at temperatures of 20° to 120° C., preferably 60° to 90° C. The polymers thus obtained can be precipitated by adding a non-solvent such as acetone, methyl ethyl ketone or methyl isobutyl ketone, or they can be sprayed as their aqueous solutions when the stability of the solutions allows.

The bis-tertiary amines of the formula (II), which can be used in the preparation of the compounds having units of formula (I) can be, for example: α,ω-N,N′-tetramethylethylene, -propylene-, -methylpropylene-, -butylene-, -butenylene-, butynylene-, -1-methylbutylene-, -hexamethylene-, octamethylene- or -decamethylenediamine or an α,ω-N-methyl-N′-alkyl-ethylene-, -propylene-, -butylene-, hexamethylene-, -octamethylene- or -decamethylene-diamine. The N′-alkyl radical is suitably one having from 1 to 12 carbon atoms, such as an ethyl, propyl, isopropyl, butyl, hexyl, octyl, decyl or dodecyl group, and preferably has from 1 to 4 carbon atoms.

The bis-tertiary amines of the formula (II), can also be heterocyclic compounds, such as N,N′-dimethylpiperazine or 4,4′-bis-(N-methylpiperidine), or unsaturated compounds such as 1,4-bis-(dimethylamino)-but-2-ene or 1,4-bis-(dimethylamino)-but-2-yne.

The bis-halogenoacyl compounds of the formula (III), which can be used for the preparation of the polymers having units of formula (I) are suitably obtained by reacting a halogenoacyl halide or a methyl or ethyl halogenoalkanoate with an α,ω-glycol, piperazine, a bis-primary diamine or urea.

The compounds of the formula (III) which may thus be obtained are compounds of the following formulae $$X—(CH_2)_n—COO—Z—OCO—(CH_2)_n—X \quad (IIIa)$$

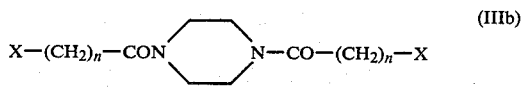 (IIIb)

$$X—(CH_2)_n—CONH—Y—NHCO(CH_2)_n—X \quad (IIIc)$$

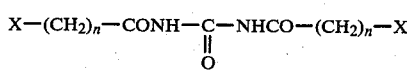

Preferred compounds of the formula (III) to be used for the preparation of the compounds of formula (I) are obtained by reacting a halogeno-acetyl-, -butyryl or -undecanoyl halide or a corresponding methyl halogenoalkanoate with: ethylene glycol, diethylene glycol, triethylene glycol, tetraethylene glycol, pentaethylene glycol, dipropylene glycol, propane-1,3-diol, 2,2-dimethyl-propane-1,3-diol, butane-1,4-diol, hexane-1,6-diol, octane-1,8-diol, decane-1,10-diol, piperazine, ethylene-, propylene, butylene-, hexamethylene-, octamethylene or decamethylene-diamine, 3,4-dithia-1,6-diaminohexane or urea.

The polyquaternary polymers containing units of the formula (I) constitute a homogeneous family of compounds which, when used in cosmetic compositions for the hair, have a conditioning effect on the hair, to which they impart springiness and gloss and make the hair easy to comb out.

These compounds are generally in the form of a white water-soluble powder.

The poly-(quaternary ammonium) polymers having units of the formula (I) indicated above can be hydrolyzed to various degrees, depending on their structure, in the presence of water or a dilute alkaline solution or in the presence of reducing agents such as thioglycolic acid.

Thus, the polymers containing units of the formula (I), in which B denotes a radical of the formula —O—Z—O— or a ureylene radical, and in which $R_1$, $R_2$, A, Z and X have the abovementioned meaning, are instantaneously degradable in dilute sodium hydroxide solution, at ambient temperature, when n denotes 1. The rate of degradation slows down as n increases.

The polymers containing units of the formula (I), in which B denotes a piperazine radical, $R_1$, $R_2$, A and X have the meaning indicated above and n denotes 1, degrade at ambient temperature in the presence of a dilute solution of sodium hydroxide, after a contact time of a few minutes to two hours.

The polymers containing units of the formula (I), in which B denotes a bis-primary diamine radical of the formula —NH—Y—NH— and $R_1$, $R_2$, A, Y and X have the above-mentioned meanings, hydrolyze in the presence of a dilute alkaline solution, at a temperature of 50° to 90° C., within a few minutes to two hours.

The compounds of this latter type, in which Y denotes the radical $-CH_2-CH_2-S-S-CH_2-CH_2-$ are also degradable by thioglycolic acid.

The poly-(quaternary ammonium) polymers having units of formula (I) therefore constitute a family of products which can be used as hair conditioners in hair compositions. Their ability to hydrolyze in the presence of alkaline solutions and, in the case of some of the products, to cleave in the presence of a reducing solution, enables them to be gradually removed during the various care and treatment processes carried out with alkaline and reducing compositions.

The compositions according to the invention can be used for treating the skin and hair. They are suitable for treating normal hair, and more particularly sensitised hair, especially in compositions of shampoos, such as anionic, cationic, non-ionic, amphoteric or zwitterionic shampoos, of coloring shampoos, of dyes, of styling gels, of styling lotions, of brushing lotions, of waveset-ting lotions, of rinses or of strengthening lotions for leave-on wavesets, or in restructuring compositions, in cosmetic treatment compositions such as anti-dandruff and anti-seborrhoea compositions, in compositions for permanently waving the hair, in treatment compositions to be applied before or after coloring bleaching or permanent waving, and in treatment lotions to be applied after straightening the hair.

In addition to the polymer which contains units of the formula (I), the cosmetic compositions according to the invention can contain any of the components conventionally used in hair compositions, such as especially anionic, cationic, amphoteric, zwitterionic or non-ionic surface-active agents, foam synergistic agents, stabilizers, opacifiers, sequestering agents, thickeners, emulsifiers, softening agents, preservatives, colorants, perfumes, cosmetic polymers and natural substances.

When the compositions according to the invention constitute shampoos, they are in the form of aqueous solutions and comprise, in addition to the polymer having units of the formula (I), at least one anionic, cationic, non-ionic or amphoteric detergent.

In these shampoos, the concentration of detergent is generally 3 to 50%, preferably 3 to 20%, by weight, relative to the total weight of the composition, and the pH is generally 3 to 9, preferably 6 to 7.

Generally, the compositions in the form of shampoos additionally contain various adjuvants, especially perfumes, preservatives, thickeners, foam stabilizers, softening agents, cosmetic resins and colorants.

Particular examples of foam stabilizers are fatty amides, in particular, the mono- or di-ethanolamides of copra fatty acids and lauryl or oleyl mono- or diethanol-amide, in amounts of 1 to 10%, preferably 1 to 3%, relative to the total weight of the composition.

Particular examples of thickeners are acrylic polymers and cellulose derivatives such as carboxymethyl-cellulose, hydroxypropylmethylcellulose and hydroxy-ethylcellulose. These thickeners are generally used in a proportion of 0.1 to 5% by weight.

Particular examples of detergents or surface-active agents which can be used in combination with the polymers having units of the formula (I) are (a) anionic surface-active agents such as alkali metal or alkanolamine salts of alkanesulphonates, alkyl-sulphates and alkyl-ether-sulphates, for example sodium alkyl-sulphates or triethanolamine alkyl-sulphates, for example where alkyl is $C_{12}$–$C_{18}$, in particular $C_{12}$–$C_{14}$, and the sodium or triethanolamine sulphates of oxethylene-ated lauryl alcohol and tetradecyl alcohol, the disodium salt of the sulphosuccinate half-ester of alkanolamides, soaps and polyether carboxylic acids;

(b) non-ionic surface-active agents such as:

(i) the products resulting from the condensation of a mono-alcohol, an alpha-diol or an alkylphenol with glycidol, for example the compounds of the formula $R-CHOH-CH_2-O-[CH_2-CHOH-CH_2-O-]_n-H$ in which R denotes an aliphatic, cycloaliphatic or arylaliphatic radical having from 7 to 21 carbon atoms, and their mixtures, it being possible for the aliphatic chains to contain ether, thioether and hydroxymethylene groups, and n is 1 to 10;

(ii) oxyethyleneated fatty alcohols having from 12 to 18 carbon atoms, for example lauryl, tetradecyl, cetyl, oleyl, palmityl or stearyl alcohol, separately or in a mixture, oxyethyleneated with 2 to 40 mols of ethylene oxide per mol of fatty alcohol;

(iii) fatty alcohols derived from oxyethyleneated lanolin, or oxyethyleneated lanolin; and (iv) the compounds of the formula $RO-[C_2H_3O(CH_2OH)]_n-H$ in which R denotes an alkyl, alkenyl or alkylaryl radical having from 8 to 30 carbon atoms and n denotes a number or a mean statistical value from 1 to 10;

(c) cationic surface-active agents such as dialkyldime-thylammonium chlorides or bromides, for example dilauryldimethylammonium chloride, alkyldimethyl-benzylammonium chlorides or bromides, alkyltrime-thylammonium chlorides or bromides, for example cetyltrimethylammonium chloride or bromide and tetradecyltrimethylammonium chloride or bromide, alkyldimethylhydroxyethylammonium chlorides or bromides, dialkyl dimethyl ammonium, chlorides or bromides, alkylpyridinium salts, for example cetylpyridinium chloride, alkylaminoethyltrimethylammonium methosulphates, imidazoline derivatives, and compounds of cationic character, for example amine oxides such as alkyldimethylamine oxides or alkylaminoethyldime-thylamine oxides; and (d) amphoteric or zwitterionic surface-active agents such as carboxylic acid derivatives of imidazole, N-alkylbentaines, N-alkylsulphobetaines, N-alkylaminobetaines, N-alkylaminopropionates, the asparagine derivatives described in our French Pat. No. 1,344,212 (U.S. Pat. Nos. 3,436,167, 3,331,781, 3,303,213, 3,257,449 and 3,738,799), alkyldimethylam-monium acetates, and ($C_{12}$–$C_{18}$) alkyldimethylcarboxyl-methylammonium salts sold as "DEHYTON A B 30" by Henkel Co.

When the compositions according to the invention constitute lotions, they are in the form of aqueous or aqueous-alcoholic solutions (suitably containing an alkanol having from 1 to 4 carbon atoms, preferably ethanol or isopropanol, in an amount of 5 to 70% by weight) and also suitably contain, in addition to the polymer having units of the formula (I), as adjuvant, one of the types of surface-active agents indicated above, preferably a cationic surface-active agent, in an amount of 0.1 to 30% by weight, relative to the total weight of the composition.

In addition to the polymer having units of the formula (I), these lotions can also contain other cosmetic polymers i.e. anionic, cationic, non-ionic or amphoteric polymers, suitably in an amount of 0.1 to 5% by weight, relative to the total weight of the composition.

Preferred cosmetic polymers or resins which can be used in combination with the polymers having units of the formula (I), are: 10% crotonic acid/90% vinyl acetate copolymers having a molecular weight of 10,000 to 70,000, vinylpyrrolidone(VP)/vinyl acetate(VA) copolymers having a molecular weight of 30,000 to 360,000, the ratio of VP:VA being between 30:70 and 70:30, quaternary copolymers of vinylpyrrolidone, having molecular weights varying from about 100,000 to about 1,000,000 such as the polymers sold as "GAFQUAT 734" and "GAFQUAT 755" by GAF Corporation, the cationic polymers resulting from the condensation of piperazine or its derivatives with bifunctional compounds such as those described in French Pat. Nos. 2,162,025 and 2,280,367 and U.S. Pat. Nos. 3,917,817 and 4,013,787, water-soluble crosslinked polyaminoamides such as those described in our French patent application No. 2,252,840 and U.S. patent application Ser. No. 762,804, filed Jan. 26, 1977, and cationic polymers derived from cellulose, such as the polymers sold as "JR" or "JR 400" by Union Carbide Corp.

The compositions according to the invention can also constitute structuring lotions which are in the form of aqueous solutions which also contain, in addition to the polymer having units of the formula (I), an agent for restructuring the hair, such as those mentioned in French Pat. Nos. 1,519,979 and 1,527,085 and U.S. Pat. No. 3,776,056, particularly methylol- or dimethylol-ethylenethiourea, in an amount of 0.1 to 5% by weight, relative to the total weight of the composition.

The compositions according to the invention can also constitute treatment creams which are in the form of an emulsion and contain, in addition to the polymer having units of the formula (I), a soap and/or a fatty alcohol such as lauryl, tetradecyl, cetyl, oleyl, stearyl or isostearyl alcohol, separately or in a mixture, in a concentration of 0.1 to 10% by weight, relative to the total weight of the composition, and an emulsifier which is a non-ionic surface-active agent, in particular a $C_{16}$ to $C_{18}$ alcohol oxyethyleneated with 6 to 40 mols of ethylene oxide per mol of alcohol, for example stearyl alcohol oxyethyleneated with 15 mols of ethylene oxide or oleyl/cetyl alcohol oxyethyleneated with 30 mols of ethylene oxide, in a concentration of 1 to 25% by weight, relative to the total weight of the composition, or anionic surface-active agents such as optionally oxyethyleneated alkyl-sulphates for example the lauryl-, cetyl- and/or stearyl-sulphate of sodium, of ammonium or of mono- or tri-ethanolamine, optionally oxyethyleneated with 2 to 40 mols of ethylene oxide per mol, such as the sodium or monoethanolamine salt of the lauryl ether sulphate oxyethyleneated with about 2 mols of ethylene oxide, these anionic surface-active agents being present in a concentration of 1 to 15% by weight, relative to the total weight of the composition.

These creams can also contain fatty amides such as the mono- or di-ethanolamides of lauric acid, oleic acid or copra fatty acids, in a concentration of 0 to 10%, and in particular 1 to 8% by weight relative to the total weight of the composition.

In addition, these creams can also contain colorants, and in particular oxidative dyestuffs and they can constitute dyeing creams or coloring creams.

The oxidative dyestuffs used as colorants may for example be direct dyestuffs, such as azo dyestuffs, anthraquinone dyestuffs, nitro derivatives of the benzene series, indamines, indoanilines or indophenols, or other oxidative dyestuffs such as the leuco-derivatives of these compounds.

Preferred oxidative dyestuffs are para- or orthophenylene- or -toluylene-diamines, nitro-para-phenylenediamines, chloro-para-phenylenediamines, meta-phenylene and meta-toluylenediamines, 2,4-diaminoanisole, meta-aminophenol, pyrocatechol, resorcinol, hydroquinone, α-naphthol, diaminopyridines and diaminobenzenes.

The colorants are generally present in amounts of 0.01 to 1% by weight relative to the total weight of the composition.

The pH of the colouring creams is generally 9 to 11 and they usually contain an alkalizing agent, for example ammonia or mono- di- or tri-ethanolamine.

The compositions according to the invention can also constitute a solution for permanent waving and can contain, in addition to the polymer having units of the formula (I), reducing agents such as thioglycolic acid or thiolactic acid, as well as an alkalizing agent and other cosmetic adjuvants such as perfumes, opacifiers and colorants.

The cosmetic compositions according to the invention suitably have a pH of 2 to 11 and contain sufficient and cosmetically effective amounts of the polymer having units of formula (I). Preferably the compositions contain 0.1 to 10% by weight of the polymers. The compositions are generally in the form of an aqueous solution, an aqueous-alcoholic solution, preferably containing an alkanol having from 1 to 4 carbon atoms, a cream, a gel, a dispersion, an emulsion or an aerosol.

When the compositions are packaged in the form of an aerosol, the propellant gas used is conventional, and is suitably carbon dioxide gas, nitrogen, nitrous oxide, a volatile hydrocarbon such as butane, isobutane or propane, or, a fluorinated hydrocarbon (sold as FREON by DuPont de Nemours) particularly those which belong to the class of the fluorochlorohydrocarbons such as dichlorodifluoromethane (Freon 12), dichlorotetrafluoroethane (Freon 114) or trichloromonofluoromethane (Freon 11). These propellants can be used by themselves or in combination and it is possible to employ, in particular, a mixture of Freon 114/12 in proportions varying from 40:60 to 80:20.

The present invention also provides a process for treating the hair or skin which comprises applying thereto a composition according to the present invention in an amount which is sufficient to condition the hair or skin.

The following Examples serve to illustrate the invention.

Table I below is intended to illustrate, in the light of Examples 8 and 18, the preparation of the polymers used in the compositions according to the invention.

This Table successively comprises information relating to the structure of the compound of the formula (II), the structure of the compound of the formula (III), the solvent used during the reaction, the reaction temperature, the heating time, the appearance of the final product isolated in accordance with the teachings of Example 8, and, finally, its absolute viscosity as a 1% w/v solution in water at 25° C.

Table II illustrates the units of the formula (I), obtained by reacting the compounds of the formulae (II) and (III) according to Table 1.

Table III relates to the properties of the polymers having units of the formula (I) and indicates the results of a test of the compatibility with an anionic surface-active agent.

It is considered that a compound having units of formula (I) has good compatibility with anionic surface-active agents when 3.5 g of this compound are completely solubilized in 250 g of a 20% w/v solution of triethanolamine laurylsulphate.

Resistance to alkaline solutions was determined with respect to a decinormal solution of sodium hydroxide and expressed in ml of 0.1 N NaOH per gram and per milliequivalent of polymer. In order to carry out this determination, 200 mg of polymer were dissolved in 20 ml of 0.1 N NaOH, at a temperature of 20° C. or 90° C., for a period of 5, 30 or 60 minutes. The residual amount of NaOH was then determined using 0.1 N HCl and the number of ml of 0.1 N NaOH consumed by the polymer was determined by difference.

The results of the tests of the compatibility with anionic surface-active agents and of the resistance to a sodium hydroxide solution are shown in Table III which comprises 5 columns. The first column identifies the polymer by the number of the example. The second column indicates the compatibility with anionic surface-active agents by a (+) sign and the incompatibility by a (−) sign. The third, fourth and fifth columns relate to the resistance to a 0.1 N solution of NaOH. The third column indicates the temperature of the solution and the contact time. The fourth and fifth columns indicate the number of ml of 0.1 N NaOH respectively consumed by 1 gram and 1 milliequivalent of polymer. The more degradable (less resistant) the polymer is in the presence of an alkaline solution, the higher is the number of ml of 0.1 N NaOH.

The polymers prepared in accordance with Examples 1 to 20 of the present application have been compared with a known reference polymer consisting of the recurring unit of the formula:

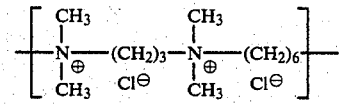

Table III indicates: (1) that all the polymers prepared in accordance with Examples 1 to 20 are compatible and that the reference polymer is incompatible with anionic surface-active agents, and (2), when subjected to the most severe conditions (30 minutes at 90° C.), the reference polymer is much less degradable by alkaline solutions (consumes much less 0.1 N NaOH) than the polymers prepared in accordance with Examples 1 to 20 of the present application.

Preparation of the compound of Example 8

130 g (1 mol) of 1,3-bis-(dimethylamino)-propane are added rapidly to a dispersion of 239 g (1 mol) of bis-(chloroacetyl)-piperazine in 500 cm³ of methanol. The reaction medium is heated at the reflux temperature of the solvent for 2 hours, while stirring. It is then turbid and very viscous. The polymer is precipitated from its solution in a large excess of acetone. After filtering and drying, a white powder is obtained. Its absolute viscosity, measured on a 1% w/v solution in water at 25° C., is 2.24 cP (centipoises).

The polymer thus prepared possesses the following recurring unit:

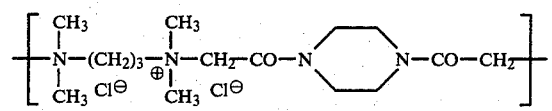

Preparation of the compound of Example 18

35.8 g (0.358 mol) of 40% w/v sodium hydroxide solution are added, at ambient temperature, to 100 ml of an aqueous solution containing 40.3 g (0.179 mol) of cystamine dihydrochloride.

40.45 g (0.358 mol) of chloroacetyl chloride and 35.8 g (0.358 mol) of 40% w/v sodium hydroxide solution are added alternately in portions to this solution, kept at between 5° and 10° C. The desired compound precipitates during the addition. The medium is stirred, at ambient temperature, for a further one hour after the addition has ended.

After filtration, washing with acetone and drying, 28 g of N,N'-bis-(chloroacetyl)-cystamine are collected. It is a white solid of melting point=117° C.

| Elementary analysis: | Calculated (%) | Measured (%) |
| --- | --- | --- |
| C | 31.47 | 31.37 |
| H | 4.5 | 4.7 |
| N | 9.18 | 9.13 |
| Cl | 23.17 | 23.26 |
| S | 20.98 | 21.17 |

6.5 g (0.05 mol) of 1,3-bis-(dimethylamino)-propane are added to 25 ml of methanol containing 15.25 g (0.05 mol) of N,N'-bis-(chloroacetyl)-cystamine and the medium is then heated for 3 hours at the reflux temperature of the solvent.

The polymer is isolated from its solution by precipitation in 200 ml of acetone.

After filtering and drying, a white powder is obtained.

The absolute viscosity, measured on a 1% w/v solution in water, is 3.58 cP.

Thin layer chromatography is used to verify that the polymer degrades instantly when brought into contact with excess thioglycolic acid in an ammoniacal medium.

TABLE I
PREPARATION OF THE POLYMERS

| Example | Compound of the formula (II) | Compound of the formula (III) | Solvent | °C. | Hours | Appearance | Absolute viscosity (centipoises) |
|---|---|---|---|---|---|---|---|
| 1 | $(CH_3)_2NCH(CH_3)CH_2N(CH_3)_2$ | $ClCH_2COOCH_2C(CH_3)_2CH_2OCOCH_2Cl$ | DMF:MC | 70 | 6 | white powder | 0.98 |
| 2 | " | " | " | 60 | 12 | " | 0.99 |
| 3 | $(CH_3)_2NCH_2CH_2CH_2N(CH_3)_2$ | $ClCH_2COO(CH_2)_3OCOCH_2Cl$ | " | 60 | 4 | " | 1.01 |
| 4 | " | $ClCH_2COOCH_2CH_2OCOCH_2Cl$ | acetone | reflux | 3 | " | 1.12 |
| 5 | " | $Cl(CH_2)_3COOCH_2C(CH_3)_2CH_2OCO(CH_2)_3Cl$ | DMF | 90 | 6 | " | 1.01 |
| 6 | " | $Br(CH_2)_{10}COO(CH_2)_2OCO(CH_2)_{10}Br$ | " | " | 3 | chestnut-colored resin | 0.96 |
| 7 | $(CH_3)_2NCH(CH_3)CH_2N(CH_3)_2$ |  $ClCH_2CON$—$NCOCH_2Cl$ | methanol | reflux | 11 | white powder | 1.62 |
| 8 | $(CH_3)_2NCH_2CH_2CH_2N(CH_3)_2$ | " | " | " | 2 | " | 2.24 |
| 9 | $(CH_3)_2N(CH_2)_{10}N(CH_3)_2$ | " | " | " | 6 | " | 1.96 |
| 10 | $CH_3\text{-}N(CH_2)_3N(C_3H_7)_2$ (branched) | " | " | " | 10 | " | 1.14 |
| 11 | $(CH_3)_2N(CH_2)_3N(CH_3)_2$ | $Cl(CH_2)_3CON$—$NCO(CH_2)_3Cl$ | DMF | 110 | 5 | " | 1.09 |
| 12 | " | $Br(CH_2)_{10}CON$—$NCO(CH_2)_{10}Br$ | DMF | 90 | 5 | soft resin | 1.07 |
| 13 | $(CH_3)_2NCH_2CH_2N(CH_3)_2$ | $ClCH_2CONHCH_2CH_2NHCOCH_2Cl$ | methanol + DMF | 90 | 7 | white powder | 1.39 |
| 14 | $(CH_3)_2N(CH_2)_3N(CH_3)_2$ | " | methanol | reflux | 3 | " | 1.94 |
| 15 | $(CH_3)_2NCH(CH_3)CH_2CH_2N(CH_3)_2$ | " | DMF | 95 | 13 | " | 1.73 |
| 16 | $(CH_3)_2NCH_2CHOHCH_2N(CH_3)_2$ | " | methanol | reflux | 5 | " | 1.09 |
| 17 | $(CH_3)_2N(CH_2)_3N(CH_3)_2$ | " | DMF | 90 | 3 | " | 0.94 |
| 18 | " | $ClCH_2CONHCONHCOCH_2Cl$ | methanol | reflux | 3 | " | 3.58 |
| 19 | $(CH_3)_2N$—$CH_2$—$CH$=$CH$—$CH_2N(CH_3)_2$ | $ClCH_2CONH(CH_2)_2$—$S$—$(CH_2)_2$—$NHCOCH_2Cl$ | water | 90 | 5 | slightly colored powder | 1.85 |
| 20 | $(CH_3)_2N$—$CH_2$—$C$≡$C$—$CH_2N(CH_3)_2$ | $ClCH_2CONH(CH_2)_2NHCOCH_2Cl$ | water | 90 | 5 | chestnut-colored powder | 1.11 |

DMF = dimethylformamide
MC = ethylene glycol monomethyl ether

TABLE II
FORMULA OF THE POLYMERS

| Example No. | CONSTITUENT UNIT OF THE POLYMER |
|---|---|
| 1 | $-[\overset{\oplus}{N}(CH_3)_2-CH(CH_3)-(CH_2)_2-\overset{\oplus}{N}(CH_3)_2-CH_2-COOCH_2-C(CH_3)_2-CH_2-O-CO-CH_2]-$ ; $2Cl^{\ominus}$ |
| 2 | $-[\overset{\oplus}{N}(CH_3)_2-CH(CH_3)-(CH_2)_2-\overset{\oplus}{N}(CH_3)_2-CH_2-COO(CH_2)_3-OCOCH_2]-$ ; $2Cl^{\ominus}$ |
| 3 | $-[\overset{\oplus}{N}(CH_3)_2-(CH_2)_3-\overset{\oplus}{N}(CH_3)_2-CH_2-COO(CH_2)_3OCOCH_2]-$ ; $2Cl^{\ominus}$ |
| 4 | $-[\overset{\oplus}{N}(CH_3)_2-(CH_2)_3-\overset{\oplus}{N}(CH_3)_2-CH_2-COO(CH_2)_2OCOCH_2]-$ ; $2Cl^{\ominus}$ |
| 5 | $-[\overset{\oplus}{N}(CH_3)_2-(CH_2)_3-\overset{\oplus}{N}(CH_3)_2-(CH_2)_3-COOCH_2-C(CH_3)_2-CH_2OCO(CH_2)_3]-$ ; $2Cl^{\ominus}$ |
| 6 | $-[\overset{\oplus}{N}(CH_3)_2-(CH_2)_3-\overset{\oplus}{N}(CH_3)_2-(CH_2)_{10}-COO(CH_2)_2OCO(CH_2)_{10}]-$ ; $2Br^{\ominus}$ |
| 7 | $-[\overset{\oplus}{N}(CH_3)_2-CH(CH_3)-(CH_2)_2-\overset{\oplus}{N}(CH_3)_2-CH_2-CON\underset{\diagup\diagdown}{\phantom{X}}NCO-CH_2]-$ ; $2Cl^{\ominus}$ (piperazine ring) |
| 8 | $-[\overset{\oplus}{N}(CH_3)_2-(CH_2)_3-\overset{\oplus}{N}(CH_3)_2-CH_2-CON(piperazine)NCO-CH_2]-$ ; $2Cl^{\ominus}$ |
| 9 | $-[\overset{\oplus}{N}(CH_3)_2-(CH_2)_{10}-\overset{\oplus}{N}(CH_3)_2-CH_2-CON(piperazine)NCO-CH_2]-$ ; $2Cl^{\ominus}$ |
| 10 | $-[\overset{\oplus}{N}(CH_3)(C_3H_7)-(CH_2)_3-\overset{\oplus}{N}(CH_3)(C_3H_7)-CH_2-CON(piperazine)NCO-CH_2]-$ ; $2Cl^{\ominus}$ |
| 11 | $-[\overset{\oplus}{N}(CH_3)_2-(CH_2)_3-\overset{\oplus}{N}(CH_3)_2-(CH_2)_3-CON(piperazine)NCO-(CH_2)_3]-$ ; $2Cl^{\ominus}$ |
| 12 | $-[\overset{\oplus}{N}(CH_3)_2-(CH_2)_3-\overset{\oplus}{N}(CH_3)_2-(CH_2)_{10}-CON(piperazine)N-CO-(CH_2)_{10}]-$ ; $2Br^{\ominus}$ |

TABLE II-continued
FORMULA OF THE POLYMERS

| Example No. | CONSTITUENT UNIT OF THE POLYMER |
|---|---|
| 13 | $\left[ -\overset{\oplus}{\underset{\underset{CH_3}{\mid}}{N}}-(CH_2)_2-\overset{\oplus}{\underset{\underset{CH_3}{\mid}}{N}}-CH_2-CONH-(CH_2)_2-NHCO-CH_2- \right]$ with $Cl^{\ominus}$, $Cl^{\ominus}$, CH$_3$, CH$_3$ |
| 14 | $\left[ -\overset{\oplus}{\underset{\underset{CH_3}{\mid}}{N}}-(CH_2)_3-\overset{\oplus}{\underset{\underset{CH_3}{\mid}}{N}}-CH_2-CONH-(CH_2)_2-NHCO-CH_2- \right]$ CH$_3$, CH$_3$, $Cl^{\ominus}$, $Cl^{\ominus}$ |
| 15 | $\left[ -\overset{\oplus}{\underset{\underset{CH_3}{\mid}}{N}}-\underset{\underset{CH_3}{}}{CH}-(CH_2)_2-\overset{\oplus}{\underset{\underset{CH_3}{\mid}}{N}}-CH_2-CONH-(CH_2)_2-NHCO-CH_2- \right]$ CH$_3$, $Cl^{\ominus}$, CH$_3$, $Cl^{\ominus}$ |
| 16 | $\left[ -\overset{\oplus}{\underset{\underset{CH_3}{\mid}}{N}}-CH_2-CHOH-CH_2-\overset{\oplus}{\underset{\underset{CH_3}{\mid}}{N}}-CH_2-CONH-(CH_2)_2-NHCO-CH_2- \right]$ CH$_3$, $Cl^{\ominus}$, CH$_3$, $Cl^{\ominus}$ |
| 17 | $\left[ -\overset{\oplus}{\underset{\underset{CH_3}{\mid}}{N}}-(CH_2)_3-\overset{\oplus}{\underset{\underset{CH_3}{\mid}}{N}}-CH_2-CONH-CO-NHCO-CH_2- \right]$ CH$_3$, CH$_3$, $Cl^{\ominus}$, $Cl^{\ominus}$ |
| 18 | $\left[ -\overset{\oplus}{\underset{\underset{CH_3}{\mid}}{N}}-(CH_2)_3-\overset{\oplus}{\underset{\underset{CH_3}{\mid}}{N}}-CH_2-CONH(CH_2)_2-S-S-(CH_2)_2-NHCO-CH_2- \right]$ CH$_3$, CH$_3$, $Cl^{\ominus}$, $Cl^{\ominus}$ |
| 19 | $\left[ -\overset{\oplus}{\underset{\underset{CH_3}{\mid}}{N}}-CH_2-CH=CH-CH_2-\overset{\oplus}{\underset{\underset{CH_3}{\mid}}{N}}-CH_2-CO-NH-(CH_2)_2-NH-CO-CH_2- \right]$ CH$_3$, CH$_3$, $Cl^{\ominus}$, $Cl^{\ominus}$ |
| 20 | $\left[ -\overset{\oplus}{\underset{\underset{CH_3}{\mid}}{N}}-CH_2-C{\equiv}C-CH_2-\overset{\oplus}{\underset{\underset{CH_3}{\mid}}{N}}-CH_2-CO-NH-(CH_2)_2-NH-CO-CH_2- \right]$ CH$_3$, CH$_3$, $Cl^{\ominus}$, $Cl^{\ominus}$ |

TABLE III
PROPERTIES OF THE POLYMERS

| Example No. | COMPATIBILITY with anionic surface-active agents | RESISTANCE TO A 0.1 N NaOH SOLUTION | | |
|---|---|---|---|---|
| | | CONDITIONS | ml of 0.1 N NaOH consumed per g. of polymer | per milli-equivalent of polymer |
| 1 | + | Contact with a 0.1 N NaOH solution for 5 minutes at 20° C. | 49.9 | 10 |
| 2 | + | | 51.8 | 9.7 |
| 3 | + | | 55 | 9.9 |
| 4 | + | | 51.6 | 8.9 |
| 5 | + | | 29 | 6.4 |
| 17 | + | | 47.6 | 8.2 |
| 20 | + | | 32.6 | 6.4 |
| 6 | + | | 26.7 | 10 |
| 7 | + | | 31.3 | 7.2 |
| 8 | + | Contact with a 0.1 N NaOH solution for 60 minutes at 20° C. | 46.5 | 8.6 |
| 9 | + | | 32.1 | 8.1 |
| 10 | + | | 45.1 | 9.6 |
| 19 | + | | 28.2 | 5.6 |
| 11 | + | | 31.2 | 9 |
| 12 | + | | 21 | 8.6 |
| 13 | + | Contact with a .01 N NaOH solution for 30 minutes at 90° C. | 78.6 | 14.4 |
| 14 | + | | 55.6 | 9.5 |
| 15 | + | | 74.9 | 13.4 |

TABLE III-continued
PROPERTIES OF THE POLYMERS

| Example No. | COMPATIBILITY with anionic surface-active agents | CONDITIONS | RESISTANCE TO A 0.1 N NaOH SOLUTION | |
|---|---|---|---|---|
| | | | ml of 0.1 N NaOH consumed | |
| | | | per g. of polymer | per milli-equivalent of polymer |
| 16 | + | | 43.4 | 7.8 |
| 18 | + | | 23.4 | 6.1 |
| Reference compound | − | Contact with a 0.1 N NaOH solution for 30 minutes at 90° C. | <5 | <0.7 |

APPLICATION EXAMPLES

EXAMPLE No. A.1

A shampoo having the following composition is prepared:

| | |
|---|---|
| Compound of Example 6 | 1 g |
| Alkyl($C_{12}$—$C_{18}$)-dimethylcarboxymethylammonium hydroxide sold under the trademark "Dehyton AB 30" by Henkel Co. | 10 g |
| Trimethylcetylammonium chloride | 1 g |
| Oxyethyleneated lauryl alcohol containing 12.5 mols of ethylene oxide | 5 g |
| Diethanolamides of copra fatty acids | 3 g |
| Perfume | |
| Colorants | |
| Water q.s.p. | 100 g |
| pH brought to 6.5 with triethanolamine. | |

EXAMPLE No. A.2

A shampoo having the following composition is prepared:

| | |
|---|---|
| Compound of Example 4 | 1 g |
| R—CHOH—$CH_2$—O($CH_2$—CHOH—$CH_2$O)$_n$H | |
| R: mixture of $C_9$—$C_{12}$ alkyl radicals | |
| n: represents a mean statistical value of about 3.5 | 10 g |
| Lauryl diethanolamide | 3 g |
| Colorants | |
| Perfume | |
| Water q.s.p. | 100 g |
| pH = 6.2 | |

EXAMPLE No. A.3

A shampoo having the following composition is prepared:

| | |
|---|---|
| Compound of Example 3 | 0.6 g |
| R—CHOH—$CH_2$—O($CH_2$—CHOH—$CH_2$—O)$_n$H | |
| R: mixture of $C_9$—$C_{12}$ alkyl radicals | |
| n: represents a mean statistical value of about 3.5 | 10 g |
| Lauryl diethanolamide | 3 g |
| Colorants | |
| Perfume | |
| Water q.s.p. | 100 g |
| pH = 7 | |

EXAMPLE No. A.4

A shampoo having the following composition is prepared:

| | |
|---|---|
| Compound of Example 2 | 1 g |
| Triethanolamine alkyl($C_{12}$—$C_{14}$)-sulphate | 10 g |
| Lauryl diethanolamide | 2 g |
| Hydroxypropylmethylcellulose | 0.2 g |
| Perfume | |
| Colorants | |
| Water q.s.p. | 100 g |
| pH = 7.0 | |

EXAMPLE No. A.5

A shampoo having the following composition is prepared:

| | |
|---|---|
| Compound of Example 18 | 1.2 g |
| Triethanolamine alkyl($C_{12}$—$C_{14}$)-sulphate | 12 g |
| Lauryl diethanolamide | 2 g |
| Perfume | |
| Colorants | |
| Water q.s.p. | 100 g |
| pH = 6.8 | |

EXAMPLE No. A.6

A shampoo having the following composition is prepared:

| | |
|---|---|
| Compound of Example 8 | 0.8 g |
| Alkyl($C_{12}$—$C_{18}$)-dimethylcarboxymethylammonium hydroxide sold by Henkel Co. under the trademark "Dehyton AB 30" | 10 g |
| Oxyethyleneated lauryl alcohol containing 12.5 mols of ethylene oxide | 5 g |
| Diethanolamides of copra fatty acids | 3 g |
| Trimethylcetylammonium chloride | 1 g |
| Perfume | |
| Colorants | |
| Water q.s.p. | 100 g |
| pH = 6.0 | |

EXAMPLE No. A.7

A shampoo having the following composition is prepared:

| | |
|---|---|
| Compound of Example 12 | 0.7 g |
| Triethanolamine alkyl($C_{12}$—$C_{14}$)-sulphate | 12 g |
| Lauryl diethanolamide | 2 g |
| Hydroxypropylmethylcellulose | 0.2 g |
| Perfume | |
| Colorants | |
| Water q.s.p. | 100 g |
| pH = 7.6 | |

EXAMPLE No. A.8

A shampoo having the following composition is prepared:

| | |
|---|---|
| Compound of Example 11 | 1.5 g |
| Sodium lauryl-sulphate oxyethyleneated with 2.2 mols of ethylene oxide | 10 g |
| Lauryl diethanolamide | 2 g |
| R—CHOH—CH$_2$—O—(CH$_2$—CHOH—CH$_2$O)$_n$H R = mixture of C$_9$–C$_{12}$ alkyl radicals n = mean statistical value of about 3.5 | 5 g |
| Perfume | |
| Colorants | |
| Water q.s.p. | 100 g |
| pH adjusted to 6 with lactic acid. | |

EXAMPLE No. A.9

A shampoo having the following composition is prepared:

| | |
|---|---|
| Compound of Example 10 | 0.6 g |
| Triethanolamine alkyl(C$_{12}$–C$_{14}$)-sulphate | 10 g |
| Lauryl diethanolamide | 2 g |
| Hydroxypropylmethylcellulose | 0.2 g |
| Perfume | |
| Colorants | |
| Water q.s.p. | 100 g |
| pH adjusted to 7 with lactic acid. | |

EXAMPLE No. A.10

A shampoo having the following composition is prepared:

| | |
|---|---|
| Compound of Example 9 | 2 g |
| Triethanolamine alkyl(C$_{12}$–C$_{14}$)-sulphate | 10 g |
| R—CHOH—CH$_2$—O(CH$_2$—CHOH—CH$_2$O)$_n$H R = mixture of C$_9$–C$_{12}$ alkyl radicals n represents a mean statistical value of about 3.5 | 5 g |
| lauryl diethanolamide | 2 g |
| Perfume | |
| Colorants | |
| Water q.s.p. | 100 g |
| pH brought to 7 with triethanolamine. | |

EXAMPLE No. A.11

A shampoo having the following composition is prepared:

| | |
|---|---|
| Compound of Example 8 | 0.8 g |
| Oxyethyleneated lauryl alcohol containing 12.5 mols of ethylene oxide | 3 g |
| Lauryl diethanolamide | 1 g |
| R—CHOH —CH$_2$—O(CH$_2$—CHOH—CH$_2$O)$_n$H R = mixture of C$_9$–C$_{12}$ alkyl radicals n represents a mean statistical value of about 3.5 | 10 g |
| Perfume | |
| Colorants | |
| Lactic acid q.s.p. pH 6 | |
| Water q.s.p. | 100 g |

EXAMPLE No. A.12

A shampoo having the following composition is prepared:

| | |
|---|---|
| Compound of Example 7 | 1 g |
| Polyglycerol lauryl ether R—CHOH—CH$_2$—O(CH$_2$—CHOH—CH$_2$O)$_n$H R = mixture of C$_9$–C$_{12}$ alkyl radicals n represents a mean statistical value of about 3.5 | 8 g |
| | 5 g |
| Lauryl diethanolamide | 2 g |
| Perfume | |
| Colorants | |
| Water q.s.p. | 100 g |
| pH 7.3 | |

EXAMPLE No. A.13

A shampoo having the following composition is prepared:

| | |
|---|---|
| Compound of Example 15 | 0.5 g |
| Triethanolamine alkyl(C$_{12}$–C$_{14}$)-sulphate | 15 g |
| Hydroxypropylmethylcellulose | 0.2 g |
| Lauryl diethanolamide | 2 g |
| Perfume | |
| Colorants | |
| Water q.s.p. | 100 g |
| pH 7.4 | |

EXAMPLE No. A.14

A shampoo having the following composition is prepared:

| | |
|---|---|
| Compound of Example 13 | 1 g |
| R—CHOH—CH$_2$—O(CH$_2$—CHOH—CH$_2$—O)$_n$H R = mixture of C$_9$–C$_{12}$ alkyl radicals n = mean statistical value of about 3.5 | 5 g |
| Diethanolamide of copra fatty acids | 3 g |
| Alkyl(C$_{12}$–C$_{18}$)-dimethylcarboxymethylammonium hydroxide sold by Henkel Co. under the trademark "Dehyton AB 30" | 10 g |
| Trimethylcetylammonium chloride | 1 g |
| Perfume | |
| Colorants | |
| Water q.s.p. | 100 g |
| pH 7. | |

EXAMPLE No. A.15

A shampoo having the following composition is prepared:

| | |
|---|---|
| Compound of Example 14 | 2 g |
| R—CHOH—CH$_2$—O(CH$_2$—CHOH—CH$_2$—O)$_n$H R = mixture of C$_9$–C$_{12}$ alkyl radicals n represents a mean statistical value of about 3.5 | 10 g |
| Polyglycerol lauryl ether | 5 g |
| Lauryl diethanolamide | 1 g |
| Perfume | |
| Colorants | |
| Water q.s.p. | 100 g |
| pH brought to 6 with lactic acid. | |

The shampoos of Examples 1 to 15 are in the form of a clear liquid. They ensure that wet hair is easy to comb out. After drying, the hair is soft, glossy and full of life.

EXAMPLE No. B.1

Wavesetting lotion

The following composition is prepared:

| | |
|---|---|
| Compound of Example 14 | 0.5 g |
| Quaternary polyvinylpyrrolidone copolymer having a molecular weight of 1,000,000, marketed under the trademark "Gafquat 734" by General Aniline Co. | of active 0.5 g material |
| Polyamino-amide (adipic acid/diethylene-triamine) crosslinked using 11 mols of epichlorohydrin per 100 basic groups | 0.5 g |
| Cetylpyridinium chloride | 0.2 g |
| Ethyl alcohol q.s.p. | 10° |
| Perfume | |
| Colorants | |
| Tartaric acid q.s.p. pH = 7 | |
| Water q.s.p. | 100 cc |

This lotion makes the hair easier to comb out, when applied to washed hair. After drying and wavesetting, the hair is soft and easy to style.

EXAMPLE No. B.2

By following Example B.1, but replacing 0.5 g of the compound of Example 14 by 0.6 g of the compound of Example 15 and adjusting the pH to 7 by means of lactic acid, a wavesetting lotion having similar properties is obtained.

EXAMPLE No. B.3

Brushing lotion

The following composition is prepared:

| | |
|---|---|
| Compound of Example 13 | 0.3 g |
| Trimethylcetylammonium bromide | 0.2 g |
| Tartaric acid q.s.p. pH 6.5 | |
| Water q.s.p. | 100 cc |

This lotion makes the wet hair easier to comb out, when applied to sensitized hair.

When the hair is styled by the brushing technique, this lotion assists the passage of the brush and leaves the hair soft and silky with a good hold.

EXAMPLE No. B.4

By following Example B.3, but replacing 0.3 g of the compound of Example 13 by 0.7 g of the compound of Example 14 and adjusting the pH to 6 by means of lactic acid, a brushing lotion having similar properties is obtained.

EXAMPLE No. C.1

Cream for oxidative dyeing

| | |
|---|---|
| Compound of Example 14 | 5 g |
| Cetyl/stearyl alcohol | 20 g |
| Oleyl diethanolamide | 4 g |
| Sodium cetyl-/stearyl-sulphate | 3 g |
| Oxyethyleneated stearyl alcohol containing 15 mols of ethylene oxide | 2.5 g |
| 22° B strength ammonia solution | 10 ml |
| Ethylenediaminetetraacetic acid sold under the trademark "TRILON B" | 1.0 g |
| Colorants: | |
| Meta-diaminoanisole sulphate | 0.048 g |
| Resorcinol | 0.420 g |
| Meta-aminophenol base | 0.150 g |
| Nitro-para-phenylenediamine | 0.085 g |
| Para-toluylenediamine | 0.004 g |
| Water q.s.p. | 100 g |

EXAMPLE No. C.2

Cream for oxidative dyeing

| | |
|---|---|
| Compound of Example 6 | 3.0 g |
| Cetyl/stearyl alcohol | 22 g |
| Oleyl diethanolamide | 5.5 g |
| Sodium cetyl-/stearyl-sulphate | 3.5 g |
| Oxyethyleneated stearyl alcohol containing 15 mols of ethylene oxide | 2.0 g |
| 22° B strength ammonia solution | 10.0 ml |
| Ethylenediaminetetraacetic acid sold under the trademark "TRILON B" | 1.000 g |
| Colorants: | |
| Meta-diaminoanisole sulphate | 0.048 g |
| Resorcinol | 0.420 g |
| Meta-aminophenol base | 0.150 g |
| Nitro-para-phenylenediamine | 0.085 g |
| Para-toluylenediamine | 0.004 g |
| Water q.s.p. | 100 g |

EXAMPLE No. C.3

Cream for oxidative dyeing

| | |
|---|---|
| Compound of Example 8 | 4.0 g |
| Cetyl/stearyl alcohol | 19.7 g |
| Oleyl diethanolamide | 4.8 g |
| Sodium cetyl-/stearyl-sulphate | 3.2 g |
| Oxyethyleneated stearyl alcohol containing 15 mols of ethylene oxide | 2.8 g |
| 22° B strength ammonia solution | 10.0 ml |
| Ethylenediaminetetraacetic acid sold under the trademark "TRILON B" | 1.000 g |
| Colorants: | |
| Meta-diaminoanisole sulphate | 0.048 g |
| Resorcinol | 0.420 g |
| Meta-aminophenol base | 0.150 g |
| Nitro-para-phenylenediamine | 0.085 g |
| Para-toluylenediamine | 0.004 g |
| Water q.s.p. | 100 g |

30 g of the cream of Example C.1, C.2 or C.3 are mixed with 45 g of hydrogen peroxide of 6% (20 volumes) strength. A smooth, thick cream is obtained which is pleasant to apply and adheres well to the hair. After waiting for 30 minutes, the hair is rinsed. The hair is easy to comb out and has a silky feel. It is set in waves and dried. The hair is glossy and full of life and has body and volume; it is easy to comb out, and has a silky feel. On 100% white hair, a blond coloration is obtained.

EXAMPLE No. C.4

Gelling ammoniacal liquid for oxidative dyeing

| | |
|---|---|
| Compound of Example 14 | 2 g |
| Triethanolamine lauryl-sulphate (40% of active material) | 4 g |
| 2-Octyldodecanol marketed under the trademark "Eutanol G" by Henkel Co. | 8 g |
| Oleyl diethanolamide | 8 g |
| Oxyethyleneated oleyl/cetyl alcohol containing 30 mols of ethylene oxide, marketed under the trademark "Mergital OC 30" by Henkel Co. | 3 g |
| Oleic acid | 21 g |
| Benzyl alcohol | 12 g |
| 96° strength ethyl alcohol | 10 g |
| 22° B strength ammonia solution | 19 ml |
| Ethylenediaminetetraacetic acid sold under the trademark "TRILON B" | 3.0 g |
| Colorants: | |
| Para-aminophenol base | 0.30 g |
| Resorcinol | 0.65 g |
| Meta-aminophenol base | 0.65 g |

-continued

| | |
|---|---|
| Para-toluylenediamine | 0.15 g |
| Sodium bisulphite solution, d = 1.32 | 1.2 g |
| Water q.s.p. | 100 g |

30 g of this formulation are mixed in a basin with 30 g of hydrogen peroxide of 6% (20 volumes) strength. A gelled, thick cream is obtained which is pleasant to apply and adheres well to the hair. It is applied using a paint-brush. After waiting for 30 to 40 minutes, the hair is rinsed. The hair is easy to comb out and has a silky feel. It is set in waves and dried. The hair is glossy and full of life and has body and volume; it is easy to comb out, and has a silky feel. On 100% white hair, a golden light blond shade is obtained.

EXAMPLE No. D.1

Hair treatment cream

| | |
|---|---|
| Compound of Example 14 | 1 g |
| Oxyethyleneated stearyl alcohol containing 2 mols of ethylene oxide, sold under the trademark "BRIJ 72" by Atlas Chemical Co. | 15 g |
| Lauryl alcohol | 2 g |
| Tartaric acid q.s.p. pH 5 | |
| Water q.s.p. | 100 g |

This cream is applied to clean, damp hair which has been towel-dried, in a sufficient amount (60 to 80 g) to thoroughly impregnate and cover the head of hair.

After waiting for 15 to 20 minutes, the hair is rinsed. The wet hair is easy to comb out and soft.

The hair is set in waves and dried under a dryer.

The dried hair is easy to comb out and has a silky feel; it is glossy and full of life and has body and volume.

EXAMPLE No. E.1

Leave-on structuring lotion

The compound of Example 14 is mixed with an equal weight of dimethylolethylenethiourea.

0.6 g of this mixture is introduced, before use, into 25 ml of water having a pH of 2.5 adjusted with hydrochloric acid.

The mixture is applied to hair which has been washed and towel-dried, before setting the hair in waves.

The hair is easy to comb out and has a silky feel.

It is set in waves and dried. The hair is glossy and full of life and has body and bulk (volume); it is easy to comb out, and has a silky feel.

EXAMPLE No. E.2

Rinse-off structuring lotion 2 g of dimethylolethylenethiourea are mixed, before use, with 25 ml of a solution containing:

| | |
|---|---|
| Compound of Example 14 | 4 g |
| Hydrochloric acid q.s. pH 2.5 | |
| Water q.s.p. | 100 ml |

The mixture is applied to hair which has been washed and towel-dried. After waiting for 10 minutes, the hair is rinsed. The hair is easy to comb out and has a silky feel. It is set in waves and dried. When dry, the hair is easy to comb out, is glossy and full of life and has body and bulk.

EXAMPLE No. F.1

Protective lotion to be applied before permanent waving

| | |
|---|---|
| Compound of Example 14 | 2.3 g |
| Tetradecyltrimethylammonium bromide | 0.13 g |
| Colorant | |
| Perfume | |
| Maleic acid q.s.p. pH 7.5 | |
| Water q.s.p. | 100 ml |

EXAMPLE No. F.2

By following Example F.1, but replacing 2.3 g of the compound of Example 14 by 2.5 g of the compound of Example 13, a composition having similar properties is obtained.

These lotions are applied to a head of hair which has been washed and towel-dried beforehand. They make the hair easier to comb out and smoother.

After permanent waving, it is found that the hair is softer and the tips, especially, remain particularly smooth. The curl strength is not changed and not reduced.

After drying, the hair does not seem to be sensitized It is glossy, smooth and very soft. This effect is particularly clear on hair which has been sensitized or coloured.

EXAMPLE No. F.3

Lotion to be applied after alkaline straightening

| | |
|---|---|
| Compound of Example 14 | 3.2 g |
| Dilauryldimethylammonium chloride sold under the trademark "Noramium M 2 C" by CECA-Prochinor Co. | 0.3 g |
| Oxyethyleneated lanoline | 1.2 g |
| Colorant | |
| Perfume | |
| Tartaric acid q.s.p. pH 6 | |
| Water q.s.p. | 100 ml |

EXAMPLE No. F.4

By following Example F.3, but replacing 3.2 g of the compound of Example 14 by 3 g of the compound of Example 15, a composition having similar properties is obtained.

The lotion F.3 or F.4 is applied to hair which has been washed and towel-dried, after alkaline straightening. It makes the hair easier to comb out, improves its softness and makes it smoother.

After drying, the hair remains smooth, glossy and soft to the touch. This effect is particularly clear on hair which has been colored or sensitized.

This lotion can also be used before each wavesetting. It makes the hair easier to comb out and improves the cosmetic appearance of the head of hair.

EXAMPLE No. G.1

Permanent waving

| | |
|---|---|
| (1) Reducing liquid: | |
| Compound of Example 14 | 1.1 g |
| Thioglycolic acid | 4 g |
| Thiolactic acid | 2 g |
| Ammonia | 4 g |

| | |
|---|---|
| Triethanolamine | 3.7 g |
| Opacifier | |
| Perfume | |
| Water q.s.p. | 100 ml |
| (2) Fixing liquid: | |
| Hydrogen peroxide q.s.p. | 7.8 volumes strength |
| Colorant | |
| Perfume | |
| Dilauryldimethylammonium chloride, sold under the trademark "Noramium M 2 C" by CECA-Prochinor Co. | 0.4 g |
| Water q.s.p. | 100 ml |

When applied to very sensitized hair, this permanent waving produces a strong curl but with a very good cosmetic condition. The hair is soft from root to tip and very glossy after drying.

We claim:

1. A cosmetic composition suitable for treating hair comprising from about 0.1 to 10% by weight of at least one poly-(quaternary ammonium) polymer having units of the formula:

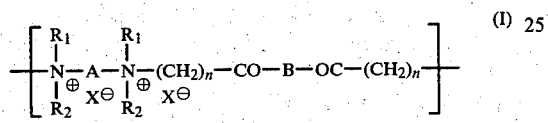

in which:
A denotes a linear or branched radical selected from the group consisting of alkylene, hydroxyalkylene, alkenylene and alkynylene having from 2 to 10 carbon atoms;
B denotes a radical selected from the group consisting of:
(a) a glycol radical of the formula —O—Z—O— in which Z denotes a linear or branched hydrocarbon radical having from 2 to 10 carbon atoms or a group of the formula:

$+CH_2-CH_2-O+_xCH_2-CH_2-$ or

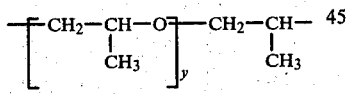

in which each of x and y denote a number of from 1 to 4;
(b) a bis-secondary diamine radical having the formula

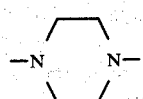

(c) a bis-primary diamine radical of the formula:

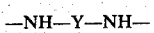

in which Y denotes a linear or branched hydrocarbon radical having from 2 to 10 carbon atoms or —CH$_2$—CH$_2$—S—S—CH$_2$—CH$_2$—; and
(d) a ureylene radical of the formula —NH—CO—NH—;

R$_1$ denotes an alkyl radical containing from 1 to 4 carbon atoms;
R$_2$ denotes a linear or branched hydrocarbon radical containing from 1 to 12 carbon atoms;
X$^\beta$ denotes a halide ion and n denotes 1 or an integer from 3 to 10; and which further comprises at least one cosmetically acceptable adjuvant and a cosmetically acceptable carrier.

2. A cosmetic composition suitable for treating hair comprising from about 0.1 to 10% by weight of at least one poly-(quaternary ammonium) polymer having units of the formula:

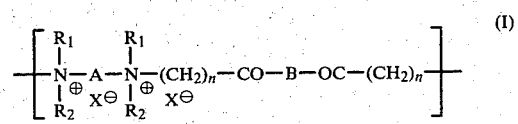

in which:
A denotes a linear or branched radical selected from the group consisting of alkylene, hydroxyalkylene, alkenylene and alkynylene having from 2 to 10 carbon atoms;
B denotes a radical selected from the group consisting of:
(a) a bis-secondary diamine radical having the formula:

(b) a bis-primary diamine radical of the formula:

in which Y denotes a linear or branched hydrocarbon radical having from 2 to 10 carbon atoms or —CH$_2$—CH$_2$—S—S—CH$_2$—CH$_2$; and
(c) a ureylene radical of the formula —NH—CO—NH—;
R$_1$ denotes an alkyl radical containing from 1 to 4 carbon atoms;
R$_2$ denotes a linear or branched hydrocarbon radical containing from 1 to 12 carbon atoms;
X$^\ominus$ denotes a halide ion and n denotes 1 or an integer from 3 to 10; and a cosmetically acceptable carrier.

3. A composition according to claims 1 or 2, in which A denotes a radical selected from consisting of an ethylene, propylene, methylpropylene, butylene, methylbutylene, hexamethylene, octamethylene, decamethylene, hydroxypropylene, butylene and butynylene radical.

4. A composition according to claims 1 or 2, in which R$_1$ denotes a methyl radical.

5. A composition according to claims 1 or 2, in which B denotes a bis-primary diamine radical of the formula —NH—Y—NH—.

6. A composition according to claim 5 in which Y denotes an alkylene radical containing from 2 to 10 carbon atoms.

7. A composition according to claim 6 in which Y denotes a radical selected from the group consisting of ethylene, propylene, 2,2-dimethylpropylene, butylene, hexamethylene, octamethylene and decamethylene.

8. A composition according to claims 1 or 2, in which B denotes a ureylene radical of the formula —NH—CO—NH—.

9. A composition according to claim 1 or 2, in which Z denotes an alkylene radical containing from 2 to 10 carbon atoms.

10. A composition according to claim 9, in which Z denotes a radical selected from the group consisting of ethylene, propylene, 2,2-dimethylpropylene, butylene, hexamethylene, octamethylene and decamethylene.

11. A composition according to claims 1 or 2 in which $X^\ominus$ denotes a chloride or bromide ion.

12. A composition according to claim 1, or 2, which is in the form of an aqueous or aqueous-alcoholic solution, a cream, an emulsion or an aerosol.

13. A composition according to claim 12 in the form of an aqueous alcoholic solution in which the alcohol is an alkanol having from 1 to 4 carbon atoms.

14. A composition according to claims 1, or 2, which has a pH of 2 to 11.

15. A composition according to claims 1 or 2 having units of the formula

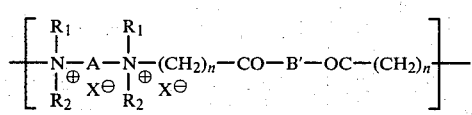
(IV)

in which B′ denotes a bis-secondary diamine radical of the formula:

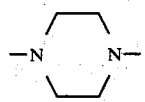

or a ureylene radical of the formula —NH—CO—NH— and n denotes 1 or an integer from 3 to 10 provided that, when B′ denotes

n denotes a number from 3 to 10 and A, $R_1$, $R_2$ and X are as defined in claims 1 or 2.

16. A composition according to claims 1 or 2 in which A is alkenylene or alkynylene.

17. A composition according to claim 1 in which: $R_1$ and $R_2$ are both $CH_3$, A is $(CH_2)_3$, B is —NH—$(CH_2)_2$—HN—, X is Cl, and n is 1.

18. A composition according to claim 2 in which: $R_1$ and $R_2$ are both $CH_3$, A is $(CH_2)_3$, B is —NH—$(CH_2)_2$—HN—, X is Cl, and n is 1.

19. The composition of claim 1, wherein the cosmetically acceptable adjuvant is selected from the group consisting of anionic, cationic, non-ionic, zwitterionic and amphoteric surface active agents, anionic, non-ionic, amphoteric and cationic polymers, foam synergistic agents, foam stabilizers, opacifiers, natural substances, perfumes, colorants, preservatives, sequestering agents, thickeners, emulsifiers and softening agents.

20. A composition according to claims 1 or 2 wherein Y denotes a —$CH_2$—$CH_2$—S—S—$CH_2$—$CH_2$ radical.

21. A composition according to claim 1 or 2, having a pH of from 5 to 7.6.

22. A shampoo consisting essentially of the polymer of claim 1 or 2, and at least one anionic, cationic, non-ionic, amphoteric or zwitterionic detergent present in from 3 to 50% by weight, relative to the weight of the entire composition, the polymer being present in from 0.1 to 10% by weight.

23. A shampoo composition comprising from 0.1 to 10% by weight of at least one poly-(quaternary ammonium) polymer having units of the formula:

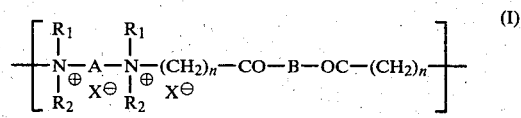

in which:
A denotes a linear or branched alkylene, hydroxyalkylene, alkenylene or alkynylene radical having from 2 to 10 carbon atoms;
B denotes:
(a) a glycol radical of the formula —O—Z—O— in which Z denotes a linear or branched hydrocarbon radical having from 2 to 10 carbon atoms or a group of the formula:

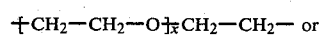

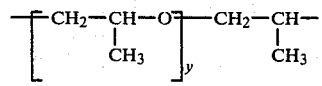

in which each of x and y denotes an integer from 1 to 4, representing a mean degree of polymerization;
(b) a bis-secondary diamine radical having the formula:

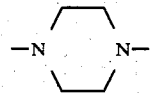

(c) a bis-primary diamine radical of the formula —NH—Y—NH— in which Y denotes a linear or branched hydrocarbon radical having from 2 to 10 carbon atoms or the divalent radical —$CH_2$—$CH_2$—S—S—$CH_2$—$CH_2$—; or
(d) a ureylene group of the formula —NH—CO—NH—;
$R_1$ denotes an alkyl radical containing from 1 to 4 carbon atoms;
$R_2$ denotes a linear or branched hydrocarbon radical having from 1 to 12 carbon atoms;
$X^\ominus$ denotes a halide ion;
and n denotes 1 or an integer from 3 to 10; from 3 to 50% by weight of at least one of an anionic, cationic, non-ionic or zwitterionic detergent; and a cosmetically acceptable carrier.

24. The shampoo composition of claim 23, wherein B denotes:
(a) a bis-secondary diamine radical having the formula:

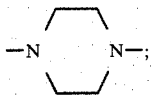

(b) a bis-primary diamine radical of the formula —NH—Y—NH— in which Y denotes a linear or branched hydrocarbon radical having from 2 to 10 carbon atoms or the divalent radical —CH₂—CH₂—S—S—CH₂—CH₂—; or (c) a ureylene group of the formula —NH—CO—NH—.

25. The shampoo composition of claim 23, wherein B denotes:

(a) a bis-primary diamine radical of the formula —NH—Y—NH— in which Y denotes a linear or branched hydrocarbon radical having from 2 to 10 carbon atoms or the divalent radical —CH₂—CH₂—S—S—CH₂—CH₂—; or (b) a ureylene group of the formula —NH—CO—NH—.

26. A shampoo according to claim 23 which has a pH of from 3 to 9.

27. A shampoo according to claim 23 which has a pH of from 6 to 7.

28. A shampoo according to claim 23 which contains an adjuvant selected from at least one of the group consisting of: perfumes, preservatives, thickeners, foam stabilizers, softening agents, cosmetic resins and colorants.

29. A shampoo according to claim 28 in which a foam stabilizer which is a fatty amide is present in an amount of from 1 to 10% by weight relative to the weight of the entire composition.

30. A shampoo according to claim 28 in which a foam stabilizer is present in an amount of from 1 to 10% by weight relative to the weight of the entire composition and is a mono- or diethanolamide of copra fatty acid, lauric acid or oleic acid.

31. A shampoo according to claim 28 in which a thickener is present in an amount of from 0.1 to 5% by weight relative to the weight of the entire composition and is an acrylic polymer, carboxymethylcellulose, hydroxyethylcellulose, or hydroxypropylmethylcellulose.

32. A lotion consisting essentially of the polymer of claims 1, 2, 17 or 18 and at least one anionic, cationic, non-ionic, amphoteric or zwitterionic surface-active agent present in from 0.1 to 30% by weight relative to the weight of the entire composition, in the form of an aqueous or aqueous alcoholic solution, the polymer being present in from 0.1 to 10% by weight.

33. A lotion according to claim 32 in the form of an aqueous alcoholic solution, in which the alcohol is an alkanol having from 1 to 4 carbon atoms, present in an amount of 5 to 70% by weight relative to the weight of the entire composition.

34. A lotion according to claim 32 which contains a cosmetic polymer other than those of formula (I) present in an amount of from 0.1 to 5% by weight relative to the weight of the entire composition.

35. A structuring lotion consisting essentially of the polymer of claims 1, 2, 17 or 18 and an agent for restructuring the hair present in from 0.1 to 5% by weight relative to the weight of the entire composition, in the form of an aqueous solution.

36. A structuring lotion according to claim 35 in which the restructuring agent is methylol- or dimethylolethylenethiourea.

37. A treatment cream consisting essentially of the polymer of claims 1, 2, 17 or 18 which contains: at least one of a soap and a fatty acid alcohol present in from 0.1 to 10% by weight relative to the weight of the entire composition; and an emulsifier selected from one of the group consisting of (a) a non-ionic surface-active agent present in from 1 to 25% by weight relative to the weight of the entire composition, and (b) an anionic surface-active agent present in from 1 to 15% by weight relative to the weight of the entire composition, the polymer being present in from 0.1 to 10% by weight.

38. A treatment cream consisting essentially of the polymer of claims 1, 2, 17 or 18 which contains at least one fatty amide selected from the group consisting of a mono-ethanolamide of lauric acid, diethanolamide of lauric acid, mono-ethanolamide of oleic acid and diethanolamide of oleic acid and mono-ethanolamide of copra fatty acid and diethanolamide of copra fatty acid in an amount of from 1 to 10% by weight of the entire composition.

39. A treatment cream according to claim 38 in which the fatty amide is present in from 1 to 8% by weight relative to the weight of the entire composition.

40. A treatment cream for coloring, which contains in addition to the composition of claim 37 a dyestuff present in from 0.01 to 1% by weight relative to the weight of the entire composition.

41. A treatment cream for coloring according to claim 40 in which the dyestuff is selected from at least one of the group consisting of oxidative dyestuffs, azo dyestuffs, anthraquinone dyestuffs, nitro derivatives of the benzene series, indoamines, indoanilines, indophenols, and the leuco derivatives of these dyestuffs.

42. A treatment cream for coloring according to claim 41 in which the oxidative dyestuff is selected from at least one of the group consisting of para- and ortho-phenylene- and toluylenediamines, chloro-para-phenylenediamines, meta-phenylenediamines, meta-toluylenediamines, 2,4-diaminoanisole, meta-aminophenol, pyrocatechol, resorcinol, hydroquinone, alpha-naphthol, diaminopyridines and diaminobenzenes.

43. A permanent waving solution consisting essentially of the composition of claims 1, 2, 17 or 18 which contains: (a) a reducing agent; (b) an alkalizing agent; and (c) at least one adjuvant selected from the group consisting of perfumes, opacifiers and colorants.

44. A permanent waving solution according to claim 43 in which the reducing agent is thioglycolic acid or thiolactic acid.

45. A process for treating hair comprising the step of applying thereto a composition comprising a cosmetically acceptable carrier and from about 0.1 to 10% by weight of at least one poly-(quaternary ammonium) polymer having units of the formula

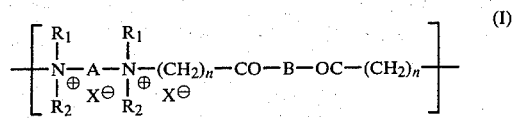

in which:

A denotes a linear or branched alkylene, hydroxyalkylene, alkenylene or alkynylene radical having from 2 to 10 carbon atoms;

B denotes:
(a) a glycol radical of the formula —O—Z—O— in which Z denotes a linear or branched hydrocarbon radical having from 2 to 10 carbon atoms or a group of the formula:

or

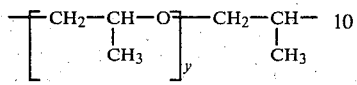

in which each of x and y denotes an integer from 1 to 4, representing a fixed degree of polymerization, or a number from 1 to 4, representing a mean degree of polymerization;
(b) a bis-secondary diamine radical having the formula:

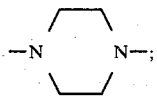

(c) a bis-primary diamine radical of the formula —N-H—Y—NH— in which Y denotes a linear or branched hydrocarbon radical having from 2 to 10 carbon atoms or the divalent radical —CH$_2$—CH$_2$—S—S—CH$_2$—CH$_2$—; or
(d) a ureylene group of the formula —N-H—CO—NH—;
R$_1$ denotes an alkyl radical containing from 1 to 4 carbon atoms;
R$_2$ denotes a linear or branched hydrocarbon radical having from 1 to 12 carbon atoms;
X$^\ominus$ denotes a halide ion;
and n denotes 1 or an integer from 3 to 10.

46. The process of claim 45, wherein the composition is a lotion and further comprises an agent for restructuring the hair present in from 0.1 to 5% by weight relative to the weight of the entire composition, said composition being in the form of an aqueous solution.

47. A process for treating hair comprising the steps of applying thereto a composition comprising a cosmetically acceptable carrier and from about 0.1 to 10% by weight of at least one poly-(quaternary ammonium) polymer having units of the formula:

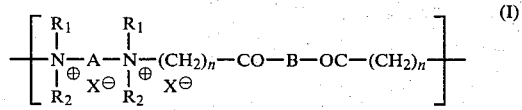

in which:
A denotes a linear or branched alkylene, hydroxyalkylene, alkenylene or alkynylene radical having from 2 to 10 carbon atoms;
B denotes:
(a) a glycol radical of the formula —O—Z—O— in which Z denotes a linear or branched hydrocarbon radical having from 2 to 10 carbon atoms or a group of the formula:

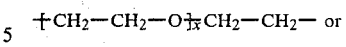

or

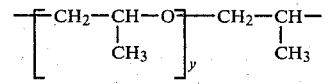

in which each of x and y denotes an integer from 1 to 4, representing a fixed degree of polymerization, or a number from 1 to 4, representing a mean degree of polymerization;
(b) a bis-secondary diamine radical having the formula:

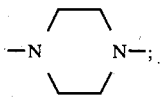

(c) a bis-primary diamine radical of the formula —N-H—Y—NH— in which Y denotes a linear or branched hydrocarbon radical having from 2 to 10 carbon atoms or the divalent radical —CH$_2$—CH$_2$—S—S—CH$_2$—CH$_2$—; or
(d) a ureylene group of the formula —N-H—CO—NH—;
R$_1$ denotes a alkyl radical containing from 1 to 4 carbon atoms;
R$_2$ denotes a linear or branched hydrocarbon radical having from 1 to 12 carbon atoms
X$^\ominus$ denotes a halide ion;
and n denotes 1 or an integer from 3 to 10; and after waiting for from about 10 to 40 minutes, rinsing and drying the hair.

48. The process of claim 47, wherein the composition is a treatment cream and further comprises at least one of a soap or a fatty alcohol present in from 0.1 to 10% by weight relative to the weight of the entire composition, and an emulsifier selected from the group consisting of (a) a non-ionic surface-active agent present in from 1 to 25% by weight relative to the weight of the entire composition, and (b) an anionic surface-active agent present in from 1 to 15% by weight relative to the weight of the entire composition.

49. The process of claim 47, wherein the composition is a treatment cream for coloring and further comprises a dyestuff present in from 0.01 to 1% by weight relative to the weight of the entire composition.

50. The process of claim 47, wherein the composition is a shampoo and further comprises from 3 to 50% by weight of at least one of an anionic, cationic, non-ionic or zwitterionic detergent.

51. The process of claim 47, wherein the composition is a lotion and further comprises at least one anionic, cationic, non-ionic, amphoteric or zwitterionic surface-active agent present in from 0.1 to 30% by weight relative to the weight of the entire composition, the composition being in the form of an aqueous or aqueous-alcoholic solution.

* * * * *

UNITED STATES PATENT AND TRADEMARK OFFICE
CERTIFICATE OF CORRECTION

PATENT NO. : 4,349,532
DATED : September 14, 1982
INVENTOR(S) : Guy Vanlerberghe, et al.

It is certified that error appears in the above-identified patent and that said Letters Patent is hereby corrected as shown below:

On the title page, before Line (21) insert:

(73) Assignee:  L'OREAL
                Paris, France

Signed and Sealed this

Second Day of July 1985

[SEAL]

Attest:

DONALD J. QUIGG

Attesting Officer          Acting Commissioner of Patents and Trademarks